United States Patent [19]

McKersie et al.

[11] Patent Number: 5,238,835

[45] Date of Patent: Aug. 24, 1993

[54] PROCESS TO INDUCE DESICCATION TOLERANCE IN SOMATIC EMBRYOS

[75] Inventors: Bryan D. McKersie, Kenilworth; Tissa Senaratna, Guelph; Steve Bowley, Guelph; J. Derek Bewley, Guelph; Daniel C. W. Brown, Nepean, all of Canada

[73] Assignee: University of Guelph, Guelph

[21] Appl. No.: 600,429

[22] Filed: Oct. 19, 1990

Related U.S. Application Data

[63] Continuation of Ser. No. 221,131, Jul. 19, 1988, abandoned.

[30] Foreign Application Priority Data

Jul. 20, 1987 [GB] United Kingdom ............... 8717099

[51] Int. Cl.$^5$ .......................... A01H 4/00; A01H 5/10
[52] U.S. Cl. ........................ 435/240.45; 435/240.4; 435/240.49; 47/DIG. 9; 47/58
[58] Field of Search .................. 47/58, 57.6, DIG. 9, 47/58.24, 57.612; 435/240.4, 240.45, 240.49, 240.5, 240.51

[56] References Cited

U.S. PATENT DOCUMENTS

| | | | |
|---|---|---|---|
| 3,920,436 | 11/1975 | Janssen | 71/65 |
| 4,615,141 | 10/1986 | Janick et al. | 47/56.6 |
| 4,777,762 | 10/1988 | Redenbaugh et al. | 47/57.6 |

OTHER PUBLICATIONS

Gray et al. (1987) In Vitro Cellular and developmental biology 23(1): 29-33.
Flick et al. (1983) in *Handbook of Plant Cell Culture*, vol. 1, Evans et al, eds. pp. 62-63.
Ammirate, ibid, pp. 106-108.
Santakumari, et al. (1987) Physiol. Plant 71:95-99.
Seedmen's Digest (Apr., 1987), vol. 38(4), pp. 6-7.
T. Senaratna et al., "Artificial Seeds of Alfalfa (Medicago Sativa L.). Induction of Desiccation Tolerance in Somatic Embryos," *In Vitro Cell Cell Dev. Biol*, 26, 85-90 (1990).
University of Guelph Department of Crop Science Annual Report (1989), (Ontario Agricultural College, Guelph, Ontario).
Norman, et al., (1983) Plant Physiol. 71:15-18.
Obendorf, et al. (1986) In Vitro, vol. 22(3):53A.
Barwale, et al. (1986) Planta 167:473-481.
Flick, et al. (1983) in *Handbook of Plant Cell Culture*, vol. 1 Evans, et al. eds., 62-63.
Santakumari, et al. (1987), Physiol. Plant 71:95-99.
Gray, et al. (1987) In Vitro Cellular & Developmental Biology (23), 29-33.

"A Surprise in the Test Tube," *Research* 5, No. 24 (1989-90) (ISSN 0841-9493).
J. Buchheim et al., "Maturation of Soybean Somatic Embryos and the Transition to Plantlet Growth," *Plant Physiol.* 89, 768-775 (1989).
W. Cheliak et al., *Can. J. Forest Res.* 20, 454 (1990).
*Stress Responses in Plants: Adaptation and Acclimation Mechanisms*, pp. 113-146, Morgan, "6. Effects of Abiotic Stresses on Plant Hormone Systems," 1990 Wiley-Liss, Inc.
*HortScience*, vol. 22(5), Oct. 1987, pp. 803-809, Redenbaugh, et al., "Encapsulation of Somatic Embryos in Synthetic Seed Coats.".
*Advanced Plant Physiology*, 1984, edited by Malcolm B. Wilkins, p. 85.
Senaratna, T. et al., "Desiccation Tolerance of Alfalfa (*Medicago Sativa L.*) Somatic Embryos. Influence of Abscisic Acid, Stress Pretreatments and Drying Rates.", *Plant Science*, vol. 65, pp. 253-259 (1989).
Van Acker, S., "A comparison of desiccation tolerance in zygotic and somatic embryos of alfalfa (*Medicago sativa L.*)," Masters Thesis, University of Guelph, Jul., 1992, (See especially p. 56).
Marsolais, A. A., et al., "Somatic embryogenesis and artificial seed production in Zonal (*Pelargonium x hortorum*) and Regal (*Pelargonium x domesticum*) geranium," *Can. J. Bot.*, vol. 69, pp. 1188-1193 (1991).
Attree, S. M., et al., "Enhanced Maturation and Desiccation Tolerance of White Spruce [*Picea glauca* (Moench) Voss] Somatic Embryos: Effects of a Non-Plasmolysing Water Stress and Abscisic Acid," *Annals of Botany*, vol. 68, pp. 519-525 (1991).

*Primary Examiner*—Che S. Chereskin
*Attorney, Agent, or Firm*—Bell, Seltzer, Park & Gibson

[57] ABSTRACT

A process for inducing desiccation tolerance in an in vitro formed plant embryo to enable production of viable artificial seeds is disclosed. The process comprises culturing in vitro plant embryos, stimulating the embryos to proceed through globular and a heart shaped stage into an elongate-torpedo shaped stage and early cotyledon stage, inducing the embryos as early as the torpedo-shaped stage with a source of abscisic acid at an effective concentration of abscisic acid and for a sufficient period of time to cause expression of desiccation tolerance which includes change in cellular metabolism, electron transport processes and oxidation-reduction reactions in the embryos and drying the induced embryos to provide stable viable embryos.

17 Claims, No Drawings

PROCESS TO INDUCE DESICCATION TOLERANCE IN SOMATIC EMBRYOS

This application is a continuation of pending application Ser. No. 07/221,131, filed Jul. 19, 1988, now abandoned.

FIELD OF THE INVENTION

This invention relates to a process to induce desiccation tolerance in tissue culture derived plant embryos for the purpose of developing artificial seeds.

BACKGROUND OF THE INVENTION

Seeds are normally the product of the sexual process. The typical seed consists of an embryo in a resting phase, incorporating and surrounded by nutritive tissues which provides for food storage and contained within a protective coat.

Some plants will regenerate asexually also. Asexual embryogenesis in vivo is a well known phenomenon in the *Rustaceae, Coctaceae, Celastraceae, Liliaceae, Myrtaceae, Orchidaceae, Rosaceae* and *Solanaceae* families. Tisserat, et al, *Horticultural Reviews*, pp. 1-99 (1979).

It is possible to produce asexual embryos in vitro. Techniques for the regeneration of plants from tissue cultures have been developed for a variety of species. This technology can be used as a means of cloning plants on a commercial scale. This would have application in processes where it is undesirable to allow the selected plants to undergo meiosis and genetic recombination to produce seeds such as in hybrid production, in propagation of elite germplasm in species which produce seeds infrequently, or in the "fixation" of genetic traits in obligate cross pollinating species. A cell from almost any part of a plant can produce an asexual embryo and from it regenerate the entire plant.

Such artificial "seeds" would substantially benefit the seed industry, agriculture, forestry and horticulture. Specific applications of such techniques include the following:

1) as a breeding tool to reduce the number of generations required to reach a seed of commerce;

2) as a means of producing hybrid seed through the propagation of parental plants such as male and female sterile plants;

3) as a means of propagating valuable agronomically superior plants for the direct establishment of production fields;

4) as a means of storing a plant in a quiescent state to synchronize planting, for transport in a sterile condition, or for long-term germplasm storage;

5) as a means of producing seed of species which flower and produce viable seed only sporadically (e.g. bamdoo).

In vitro asexual embryogenesis techniques produce an embryo, which is identical in most respects to a normal zygotic embryos. These embryos lack a surrounding endosperm and the latter being derived exclusively from maternal tissue in the zygotic seed. Another distinct difference between the two types of embryos is that asexual embryos cannot be dried and stored for any period of time. There are two ways to protect the embryos from drying: they can be coated with compounds which prevent the loss of water (i.e. avoid drying) or alternatively, they can be induced to tolerate drying by synthesizing protective chemicals which protect the cells from the consequences of water loss. Previous methods have emphasized ways of reducing water loss and certain coating techniques have been developed. Edward W. Janssen describes in his U.S. Pat. No. 3,920,436 a process that creates an artificial protective environment for plants by coating a portion of the plant with a fluid agent comprising hydrophilic urethane prepolymer. However, this system is designed for the protection of mature plants by preventing water loss and since the prepolymer is insoluble, it would not allow the embryo to germinate.

Wet capsules have been used to replace the seed coat. Plant Genetics Inc. (PGI) has developed a process for gel coating somatic embryos to help withstand the rigors of handling and field planting. The coating is comprised of two parts: a matrix containing essential nutrients etc. and a protective polymer seed coat which prevents desiccation. The resulting capsules are about the size of soya bean seeds, spherical in shape and thus adaptable to large scale agricultural use. However, there are disadvantages in such a wet capsule. The capsules need special low temperature storage conditions otherwise they will start to germinate prematurely making long-term storage impossible. The vigor of seedlings may also be reduced due to the avoidance of the natural drying process.

Janick and Kitto describe in their U.S. Pat. No. 4,615,141 certain methods for enhancing desiccation tolerance in somatic embryos The asexual embryos are "hardened" by various means during their development to induce resistance to environmental stress. The hardened asexual embryos are then coated with a solution of non-toxic biocompatible, water soluble synthetic coating material. The resulting solution-coated embryos are then dried to provide viable embryos encapsulated in the coating material. Embryos encapsulated by this method are relatively short-lived in the dry state (ca. 2-4 days).

Janick and Kitto described four separate hardening treatments: high inoculum density, high sucrose concentrations, chilling and/or exposure to abscisic acid (ABA). Each of these pretreatments enhances the viability of the embryos after encapsulation. These treatments increase synthesis of ABA, a plant growth regulator. It would appear that ABA is a factor in the survival of somatic embryos. The type of hardening treatment used is critical since it renders asexual embryos quiescent and induce the endogenous synthesis of specific protectants, such as oxygen-free radical scavengers, thereby increasing the survival rate of the embryos following desiccation.

Tolerance of desiccation has at least two components. The first is tolerance to the loss of water, and the second is the ability to maintain viability during prolonged periods of dryness. Tolerance to the loss of water can be induced in plant tissues by the induction of quiescence or dormancy. Tolerance of prolonged storage is provided in part by high levels of lipid soluble free radical scavenging systems (antioxidants), such as tocopherol. Both components of desiccation can be induced by ABA, but the response of the embryo is dependent on the stage of development at the time of treatment. Quiescence can be induced at a wide range of developmental stages, but the induction of antioxidant synthesis is accomplished only at specific stages. In the method of Janick and Kitto, the ABA treatment was not applied at the correct stage of development to induce synthesis of antioxidants. This would explain why their embryos could not survive drying without coating and why the coated embryos survived only 2 to 4 days.

SUMMARY OF THE INVENTION

According to an aspect of the invention, the process for inducing desiccation tolerance in an in vitro formed plant embryo to enable production of viable artificial seeds comprises culturing in vitro plant embryos, then stimulating the embryos to proceed through globular and a heart shaped stage into an elongate-torpedo shape stage, and early cotyledon stage. The embryos are induced as early as the torpedo shaped stage with the source of abscisic acid at an effective concentration of abscisic acid and for a sufficient period of time to cause expression of desiccation tolerance which includes change in cellular metabolism, electron transport processes and oxidation-reduction in the embryos. The induced embryos are dried to provide stable viable artificial seeds.

According to preferred aspects of the invention, the source of abscisic acid is developed by application of an environmental stress to cause the embryos to synthesize abscisic acid, exogenous application of abscisic acid or exogenous application of alternative chemicals which trigger production of ABA, i.e., inducing the embryos with inhibitors of isoprenoid metabolism.

DETAILED DESCRIPTION OF THE PREFERRED EMBODIMENTS

There are a wide variety of means by which plant tissues can be cultured on artificial growth media in sterile conditions and induced to form embryos with organized meristematic tissues. There are two species used as examples to demonstrate this invention, but the principles will apply to most plant embryos developing under in vitro culture conditions. Once the embryos are stimulated to form from the original plant tissue they proceed through a development sequence similar in many respects to those observed in zygotic embryos in vivo.

After the embryos are formed their development proceeds through a globular and heart-shaped stage into an elongated torpedo stage with distinct apical and root meristems and rudimentary cotyledons. As early as the torpedo stage, the embryo is capable of being induced by the proper environmental or chemical signals to develop tolerance of desiccation. Without these signals, desiccation tolerance will not be expressed. Furthermore, if the signals are applied at the incorrect stage of development, the tissue will not respond properly. The appropriate stage is a broad time frame, the optimum being approximately between the torpedo to cotyledonary stages of development. The exact timing of the signal to cause expression of desiccation tolerance will vary between species, media, growth conditions, and temperature, all of which influence the embryos rate and type of development.

The signal applied to the embryo to induce the expression of tolerance may also vary, but involves either the exogenous application of a plant growth regulator, abscisic acid (ABA), or the application of an environmental stress, or similar signal, which causes the plant to synthesize ABA. The exogenous application of ABA is in most instances the most efficient means of inducing expression of desiccation tolerance. The preferred method for the exogenous application of ABA is by indirect techniques, for example on a solid agar media on which the embryos are placed, separated from the media by a nylon paper or similar mesh and a thin layer of callus, preventing direct contact between the embryos and ABA-containing media. Growing embryos on a mesh has other advantages. It facilitates easy handling of embryos. Embryos can be moved from one media to another with the mesh, without disrupting the microenvironment and polarity which has already developed.

Numerous environmental stresses also can be used to induce the embryo at this stage of development to express desiccation tolerance, as a result of ABA synthesis by the embryo. These stresses include a slow gradual desiccation over several days, low temperatures, deprivation of nutrients, deprivation of water or osmotic stresses and nonlethal heat stress. It is appreciated that any chemical which causes the synthesis or accumulation of ABA would have similar effects.

Thus, there are two major principles in this process. First is the development of the embryo to the proper stage of development. Second, is the exposure to the growth regulator, ABA.

The application of ABA initiates a distinctly different developmental pattern in the tissue culture-derived embryo, which is similar in many respects to that of a zygotic embryo. This process culminates in the inhibition of cellular metabolism and suppression of electron transport processes and oxidation-reduction reactions. If the tissues were dried without these metabolic processes being suppressed, they might be expected to cause the formation of deleterious agents, such as oxygen free radicals. The tissue at the same time accumulates a number of cellular membrane stabilizing agents, such as low molecular weight carbohydrates and lipid soluble antioxidants, such as tocopherol.

ABA synthesis involves the isoprenoid pathway. Although the structure of ABA had been known since 1965, the detailed pathway of ABA synthesis in higher plants has remained obscure. Research has focused on two pathways; (1) the direct pathway involving a $C_{15}$ precursor derived from farnesyl pyrophosphate and (2) the indirect pathway involving a precursor derived from a carotenoid. The relative importance of each pathway is unknown, and the possibility exists that both pathways operate at the same time as described in Zeevart and Creelman, 1988, Metabolism and Physiology of Abscisic Acid. *Ann. Rev. Plant Physiol. and Plant Molec. Biol.* 39:439-473. In either case it is suggested that mevalonate is the ultimate precursor.

Treatment of plants with certain chemicals increases ABA levels in plant tissues. For example, triazoles have been shown to increase endogenous ABA levels and it was suggested that triazoles selectively inhibit certain reactions in the isoprenoid pathway and this inhibition may have resulted in increased ABA levels. Other chemicals such as mefluidide are also known to increase ABA levels in plant tissues.

Whatever the metabolic pathway may be, certain environmental stresses induce ABA synthesis in plant tissues.

The ABA levels have been shown to increase in tissues (fruits, leaves, phloem exudates) of water stressed plants. Flooding increased the ABA level by 10 fold with no leaf water deficit. It was suggested that the flooding inhibited the shoot to root translocation and that caused the ABA to accumulate. Interesting results have been reported in *Dunaliella parva*. This salt tolerant alga had its lowest ABA content at 1.5M NaCl, the medium that is optimum for its growth and photosynthesis. Lower and higher NaCl levels increased the amount of ABA in cells as well as in the medium. Transient increase in ABA content in plant tissue has also occurred when exposed to low temperatures during cold hardening.

It has also been reported that the plants pre-exposed to drought, mineral deprivation or salination had elevated ABA levels.

Once tolerance has been induced, the embryo can be air dried to moisture contents less than 20% water, or equivalent to those observed in true seeds. Drying can be done slowly by transferring the embryos to successively low relative humidity environments over a period of several days, but if tolerance has been properly induced, the embryos can be rapidly dried in the air within approximately 24 hours.

Once dried, the embryos can be stored for prolonged periods of time, up to several months in atmospheric conditions at room temperature. If the dried embryos are stored in a cool, dry condition, such as those used to store true seed, the embryos could be stored successfully for several years with minimal loss of viability, similar to that observed in true seeds.

The dried embryos can be rehydrated in water on germination paper or directly planted into peat or soil. Once rehydrated, the developmental pattern of the "seedling" follows that observed during the germination of a true seed, namely radical emergence, development and expansion of the primary leaf, shoot and root. It is not necessary to rehydrate the dried embryo on nutrient and root media such as that on which it initially developed. The growth rate of seedlings from dried embryos is approximately twice that observed for embryos which have not been dried. The reason for this is probably similar to that observed in true seeds, in which desiccation itself acts as a developmental switch between anabolic and catabolic processes.

The survival of the desiccation treatment per se of this invention approaches 100%. For example, when embryos are pre-selected, based on visual morphological development and dried using our process, the survival rate was 100% after desiccation. Lower success rates can usually be attributed to improper embryo formation prior to the desiccation phase and reflect less than optimum initial embryo formation. If nutrient or growth regulator levels during the early phase of culture are not optimum, some may be misformed and although they may survive the desiccation treatment will not establish seedlings.

Asexual plant embryogenesis techniques are well known in the art. The alfalfa line A70-34 is selected as one example for the evelation of desiccation tolerance in accordance with this invention because it has high frequency of embryogenesis. As previously noted, the desiccation technology of this invention is useful with any plant species which can produce embryos in a cell culture system.

EXAMPLE 1

Petiole sections from fully expanded leaves of alfalfa are used to initiate calli of B5h media following sterilization (Table 1). The calli are then transferred onto GB5 media for cell multiplication. Three predominant cell types exist in an alfalfa cell suspension culture: large clumps of non-differentiated cells and abnormal somatic embryos; small cell clusters composed of non-differentiated meristematic cells; and large "banana" shaped, single cells. It is believed that the small cell cluster composed of non-differentiated meristematic cells gives rise to somatic embryos. The larger aggregates are removed by screening the suspension through 1000 or 500 um nylon mesh. Subsequent filtering through 200 um mesh collected some single cells and selected the meristematic small cell clusters. This filtration serves to enrich the culture for embryogenic cells and to synchronize embryo development.

Cells are plated on a nylon mesh and for ease of handling placed on solid Bi2y agar media (Table I). The embryos develop in a synchronized fashion on the nylon mesh. According to this invention, these nylon filters are placed on nutrient media without plant growth regulators (Bi2Y) for 10 to 14 days.

According to this invention, the embryos are then transferred to the same media, but containing ABA. The timing of the ABA treatment is very important, as previously discussed. For example, Janick and Kitto in their U.S. Pat. No. 4,615,114 subject the embryos to the ABA treatment during the stimulation phase, as opposed to after it. Such differences in the timing of the ABA treatment can produce considerable changes in the viability of the treated embryos. Then later, after stimulation but before precocious germination, the embryos are subjected to the ABA treatment, the better the resistance to desiccation. Embryos between the ages of 9 to 18 days after stimulation respond best to concentrations of ABA between 5 to 10 uM applied for 5 to 14 days.

According to this invention after 5–14 days of ABA treatment, the embryos are dried. Two different drying regimes are used: "fast" and "slow" drying. Fast drying is achieved either by air drying or in a low humidity (43% relative humidity) chamber. Under this regimen embryos are dried to as low as 7.4% moisture w/w within a day. Slow drying is achieved by placing embryos in a series of desiccators with controlled humidity for six days. For the first day of drying, embryos are kept at 97% humidity and are transferred daily to chambers with 87%, 75.5%, 62.5%, 50.5% and finally to 43% relative humidity.

TABLE 1

| Nutrient | GB | B5h | Bi2Y |
|---|---|---|---|
| KNO₃ | 25.0 mM | 30.0 mM | 10.0 mM |
| CaCl₂.2HO | 1.0 | 6.0 | — |
| MgSO₄.7H₂O | 1.0 | 2.0 | 0.14 |
| (NH₄)SO₄ | 1.0 | 1.0 | — |
| (NH₄)2HC₆H₅)₇ | — | — | — |
| NH₄H₂PO₄ | — | — | — |
| NH₄NO₃ | — | — | 12.0 |
| NaH₂PO₄.H₂O | 1.1 | 1.1 | — |
| KCl | — | — | 0.9 |
| Ca(NO₃)₂ | — | — | 2.0 |
| KH₂PO₄ | — | — | 2.2 |
| KI | 4.5 uM | 4.5 uM | 4.8 uM |
| H₃BO³ | 48.5 | 48.5 | 26.0 |
| MnSO₄.H₂O | 59.2 | 59.2 | 26.0 |
| ZnSO₄.7H₂) | 7.0 | 7.0 | 5.2 |
| Na₂MoO₄.2H₂O | 1.0 | 1.0 | — |
| CuSO₄.5H₂O | 0.1 | 0.1 | — |
| CoCl₂.6H₂O | 0.1 | 0.1 | — |
| FeEDTA (330 FE) | 43 mg/l | — | 32 mg/l |
| Na₂EDTA | — | 0.13 mM | — |
| FeSO₄.7H₂O | — | 0.10 mM | — |
| myo-inositol | 0.55 uM | 0.55 mM | 0.55 mM |
| nicotinic acid | 8.1 uM | 8.1 uM | 4.1 uM |
| pyridoxine HCl | 4.9 | 4.9 | 0.5 |
| thiamine HCl | 29.6 | 29.6 | 0.3 |
| adenine | 7.4 uM | 7.4 uM | — |
| L-glutamine | 5.5 mM | 5.5 mM | — |
| L-glutathione | 33.0 uM | 33.0 uM | — |
| L-serine | 1.0 mM | 1.0 mM | — |

TABLE 1-continued

| Nutrient | GB | B5h | Bi2Y |
|---|---|---|---|
| l-proline | — | — | — |
| glycine | — | — | 26.6 uM |
| sucrose | 60 mM | 90 mM | 90 mM |
| Auxin: 2,4-D* | 1.0 mg/l | 1.0 mg/l | — |
| NAA | 0.1 mg/l | — | — |
| Kinetin | — | 0.2 mg/l | — |
| GA$_3$ | — | — | — |
| Agar or agarose | 0.9% | 0.9% | 1.0% |
| pH | 5.5 | 5.5 | 5.8 |

The embryos are then allowed to equilibrate with air. At this stage, the embryos can be stored. No encapsulation is necessary.

EXAMPLE 2

Table II shows the survival rate of ABA treated embryos after "fast" or "slow" drying. Embryos treated with ABA were tolerant to desiccation after fast or slow drying. Survival after desiccation (conversion to plants) was as high as 80%.

TABLE II

Survival of ABA treated embryos after fast or slow desiccation

| | Means of 2 experiments | | | | | |
|---|---|---|---|---|---|---|
| Embryo age | 11 days | | 14 days | | 18 days | |
| Drying regime | Fast | Slow | Fast | Slow | Fast | Slow |
| ABA conc. um | | | % survival | | | |
| 0 | 8 | 46 | 24 | 44 | 15 | 43 |
| 5 | 51 | 54 | 53 | 80 | 65 | 69 |
| 10 | 58 | 47 | 68 | 64 | 69 | 59 |

This invention has a significant advantage over the treatment proposed by Janick et al., whereby the embryos are dried only after the embryos have been contacted with the encapsulating material. On the other hand, the treatment, according to this invention, involving use of ABA followed by drying treatment creates an embryo that is more like a true seed. The embryos once mature and dry can be planted directly into sterilized soil in the greenhouse. This is unlike Janick et al. where their measure of viability of embryos is by growth on sterilized nutrient media in culture. Growth of embryos on such stabilized nutrient media in culture is much more costly and time consuming than planting directly into sterilized soil.

Embryos subjected to the treatment with ABA and drying according to this invention have 60-75% conversion rates into intact plants. The results are more consistent than those produced by embryos subjected to the treatment described by Janick and Kitto. The failure of some embryos to recover following the drying treatment is the result of poor quality embryo formation initially. Survival would approach 99 to 100% if preferably embryos are preselected prior to drying.

Embryos developed by the methods contemplated by this invention have been stored in an open atmosphere for as long as eight months. This compares very favorably to a complete loss of viability in embryos treated in the Janick and Kitto method. The longer survival time provided by this invention has direct commercial consequences in shipping and storage. The embryos could be stored for prolonged periods in similar systems used for long term seed storage. Such methods of storage would provide a valuable bank of genetic material and enable easy transportation of embryos for prolonged periods.

According to this invention, treatment by ABA of asexually produced embryos after the induction phase followed by a drying regimen creates artificial seeds of enhanced viability. Although no encapsulation is required, a capsule containing nutrients, fungicides, etc. may benefit the embryos once growth has begun.

It is also appreciated that other techniques may be employed to induce ABA synthesis in the embryo. Such synthesis may be induced by including triazole compounds, such as triadimefon. Environmental stress will also induce ABA synthesis such as the previous slow drying procedure (Table II), gradual mild water stress, cold stress and nutrient stress. Mild water stress is achieved by allowing the solid agar media containing embryos to dehydrate slowly, such as by use of high osmotic media to induce dehydration. Cold stress may be imposed by placing agar plates containing embryos in controlled environmental chambers.

EXAMPLE 3

Temperatures between 2° to 6° C. have been investigated as set out in the following Table III. TABLE III. Effect of cold treatment on desiccation tolerance of embryos. 14 day old embryos were cold treated at 2° to 4° C. for two weeks.

TABLE III

| | % Survival | |
|---|---|---|
| | Fast Drying | Slow Drying |
| Expt. 1 | 0 | 60 |
| Expt. 2 | 20 | 54 |

EXAMPLE 4

Nutrient starvation may be achieved by placing the fully grown embryos on media with reduced nutrient levels compared to the media in which they were grown before. The results of nutrient deprivation are shown in Table IV.

TABLE IV

Effect of nutrient deprivation on desiccation tolerance of somatic embryos of alfalfa.

| | % Survival | |
|---|---|---|
| | Fast Drying | Slow Drying |
| Control Bi2Y media | 0 | 0 |
| Full sucrose + ½ salts | 16 | 52 |
| Full sucrose + ¼ salts | 0 | 81 |
| Full sucrose + 1/10 salts | 0 | 14 |

EXAMPLE 5

The effect of slow drying of somatic embryos on increasing their desiccation tolerance is shown in the following Table V.

TABLE V

Effect of slow drying (unsealed) of somatic embryos in agar media, on their desiccation tolerance.

| | Days on Bi2Y | | |
|---|---|---|---|
| | 18 | 23 | |
| | % survived | | Mean |
| Control | | | |
| slow drying | 15 | 36 | |
| | | | 20 |
| fast drying | 15 | 17 | |
| Unsealed | | | |
| slow drying | 35 | 54 | |
| | | | 54 |

TABLE V-continued

Effect of slow drying (unsealed) of somatic embryos in agar media, on their desiccation tolerance.

| | Days on Bi2Y | | |
|---|---|---|---|
| | 18 | 23 | |
| | % survived | | Mean |
| fast drying | 67 | 60 | |

The inclusion of ABA in the growth media or alternatively exposure to any environmental or chemical agent which induces the synthesis or accumulation of ABA clearly induces somatic embryos to develop tolerance of desiccation to levels of low water contents. The inclusion of any chemical in the growth media or exposure to an environmental condition which induces the synthesis or otherwise increases the lipid soluble antioxidant content of cellular membranes or the quantity of other membrane stabilizing agents also induces similar degrees of desiccation tolerance.

Alfalfa Cell Culture System

Additional examples are provided to describe other aspects of the invention with respect to mediums used in cultures, conditions of signaling desiccation tolerance and application of invention to other plant varieties. Most of the experiments described in the following examples used the alfalfa cell culture system as a model system. The principles involved in the process are broadly applicable to other systems which form embryos or similar organized meristematic tissue, albeit with slightly different optimum treatment conditions. The alfalfa cell culture system described here is presented for information and is not an obligate part of the process for induction of desiccation tolerance.

Preparation

Callus cultures are initially formed from sterile sections of petiole tissue from a donor plant. Specific cell lines of alfalfa are used which carry gene(s) coding for regeneration capacity. These genes originated from an alfalfa plant from the cultivar Rangelander coded as A70-34, and have been transferred by conventional plant breeding methods into other lines. Selection of the donor plant is very important for the production of large quantities of high quality somatic embryos. The media used for the initial callus formation called B5h, (Table VI) contains 1.0 mg/L 2,4-D as an auxin source. This plant growth regulator stimulates embryo initiation. After a certain mass of callus is formed, which in accordance with this embodiment occurs 14–21 days after the initial culturing, the callus is transferred to a liquid media, GB5 (Table VI), which also contains 2,4-D. This media serves to break the mass of callus into small fragments and allows further cell multiplication and embryo initiation. Three predominant cell types exist in this suspension culture: large clumps of non-differentiated cells and abnormal somatic embryos; small cell clusters composed of non-differentiated meristematic cells, which under appropriate conditions develop into globular embryos; and large "banana" shaped single cells, which are terminally differentiated. These classes of cells are separated by screening the suspension through first a 500 um nylon mesh and then a 200 um mesh. The latter screen contains the small clusters of cells which are more or less synchronized in their development of somatic embryos. Thus, this filtration step serves to enrich the culture for embryogenic cells and to synchronize embryo development.

TABLE VI

Chemical Composition of Tissue Culture Media

| | Weight (mg/liter) | | |
|---|---|---|---|
| Chemical | Bi2Y' | GB5' | B5h' |
| Macronutrients: | | | |
| NH4NO3 | 1,000 | | |
| KCl | 65 | | |
| KNO3 | 1,000 | 2,500 | 3,000 |
| CaCL2.2H2O | | 150 | 895 |
| Ca(NO3)2 | 347 | | |
| MgSO4 7H2O | 35 | 250 | 500 |
| KH2PO4 | 300 | | |
| (NH4)2SO2 | | 134 | 134 |
| NaH2PO4.H2O | | 150 | 150 |
| Micronutrients: | | | |
| KI | .8 | .75 | .75 |
| H3BO3 | 1.6 | 3 | 3 |
| MnSO4.H2O | 4.4 | 10 | 10 |
| ZnSO4.7H2O | 1.5 | 2 | 2 |
| Na2MoO4.2H2O | | .25 | .25 |
| CuSO4.SH2O | | .025 | .025 |
| CaCl2.6H2O | | .025 | .025 |
| Na2.EDTA | | | 37.3 |
| Na.Fe.EDTA | 32 | 43 | |
| FeSO4.7H2O | | | 27.3 |
| Amino Acids: | | | |
| Adenine | | | 1 |
| Glycine | 2 | | |
| L-glutamine | | | 800 |
| L-Glutathione | | | 10 |
| Serine | | | 100 |
| Vitamins: | | | |
| Myo-inositol | 100 | 100 | 100 |
| Nictonic acid | .5 | 1 | 1 |
| Pyridoxine HCl | .1 | 1 | 1 |
| Thiamine HCl | .1 | 10 | 10 |
| Sucrose | 30,000 | 20,000 | 30,000 |
| Yeast Extract | 2,000 | | |
| Agar | 9,000 | | 9,000 |
| Hormones: | | | |
| 2,4-D | | 1 | 1 |
| Kinetin | | | .2 |
| NAA | | 0.1 | |
| pH | 5.8 | 5.5 | 5.5 |

To allow the continued development of the somatic embryos, the fraction enriched with embryogenic cells collected on the 200 um screen is spread into a thin layer and placed with the screen onto a hormone-free media, Bi2Y (Table 1). After approximately 4 days future embryos are visible as green dots. After approximately 7 days, green heart shaped embryos are apparent protruding from the bed of callus in a more or less synchronized stage of development.

It is recognized that a wide variety of procedures can be used to produce embryos from plant tissues with a certain degree of synchrony. Any of these procedures would be satisfactory provided that the embryos are of "high quality" meaning similar in form to zygotic embryos, and capable of forming a seedling with roots and shoots and no tendency to form callus spontaneously.

In the tissue culture procedure described in the previous section, 5 alfalfa petiole sections (25 mg weight) are used per petri plate. The callus from these 5 sections is used to inoculate 1 flask of suspension culture (25 ml), which is then used to prepare 10 nylon disks (one disc is about 7 cm² size). Each nylon disk produces about 150 embryos (best result=220) in two waves of development: the first wave is the one used for further work and contains about 60% of the total or 90 embryos (best result=132) per nylon screen. At this stage, there are 900 (best result=1320) somatic embryos produced per 5 petiole sections. This represents a rate of embryo formation of 36,000 embryos (best result=52,800) per g of petiole tissue, which is a highly embryogenic system compared to other species. A conservative estimate is that 60% of the somatic embryos will convert successfully into plants, regardless of whether they are desiccated or not, yielding 21,600 plants per g of petiole.

It would take approximately 160 petiole sections or 80 full petioles to yield 1 g of donor tissue. Using 3 petioles from a stem of an alfalfa plant with a total of 10 stems would yield 60 sterilized petiole sections (0.30 g). Thus, 1 alfalfa plant could be expected to yield 6,500 regenerated plants in 1 cycle of the cell culture system. The total time involved in this cycle approaches 3 months.

EXAMPLE 6

Effect of stage of development, and ABA concentration on the survival of alfalfa embryos following drying.

There is an optimum stage of development and an optimum concentration of ABA which elicits a response in the embryo which leads to the expression of desiccation tolerance. This optimum would be expected to vary between species and culture conditions. On this example, somatic embryos were formed as described in the preceding procedure. At 11, 14 and 18 days after transfer to Bi2Y media (corresponding to torpedo, early cotyledon and mid cotyledon stages of development), the embryos were transferred on the nylon screen to Bi2Y media containing 0, 5 or 10 u Molar concentration of ABA for 5-14 days. The embryos were subsequently dried in the air and viability determined, 1 week later, by the ability of the embryos to grow upon rehydration into plants.

TABLE VII

| | Survival of alfalfa somatic embryos following air drying | | |
|---|---|---|---|
| ABA Concentration $10^{-6}$ Molar | Embryo age (days) | | |
| | 11 | 14 | 18 |
| | % regrowth | | |
| 0 | 8 | 24 | 15 |
| 5 | 51 | 53 | 65 |
| 10 | 58 | 68 | 69 |

The optimum stage of development is relatively broad, influenced to some degree by the synchrony of embryo development. Some desiccation tolerance was induced in the absence of ABA, but 5 to 10 uM concentrations promoted higher survival of the somatic embryos. The relatively low (50-70%) regrowth of the embryos in the above data is primarily a result of the quality of the embryos prior to drying, and not necessarily the drying process per se. If good quality embryos are preselected the survival rate approaches 100% (Table VIII). Further experiments have shown that concentrations of ABA in the range of 10-3 Molar are toxic to the plant tissue and are therefore unsatisfactory. Furthermore, concentrations in the range of $10^{-8}$ molar are ineffective.

TABLE VIII

| Survival (% regrowth) of preselected embryos following air drying | | |
|---|---|---|
| ABA concentration | Embryo age (days) | |
| ($10^{-6}$ molar) | 11 | 14 |
| 10 | 87-100 | 94-97 |

EXAMPLE 7

Effect of Embryo Developmental Stage on Sensitivity to ABA Induction of Desiccation Tolerance Alfalfa somatic embryos were induced as detailed above and transferred to hormone free Bi2y'. At specified days of growth on Bi2y' media the embryos were transferred to Bi2y media containing 10-5 M ABA (10 umolar) for a period of 7 days. The embryos were subsequently dried and rehydrated in germination paper to estimate viability as in Example 6.

TABLE IX

| Response of embryos at different stages of development to ABA treatment. | | | | | | | |
|---|---|---|---|---|---|---|---|
| | Embryo age (days) | | | | | | |
| | 3 | 5 | 6 | 7 | 9 | 12 | 13 | 15 |
| | % viability | | | | | | |
| Experiment 1 | 0 | 0 | — | 74 | — | — | 92 | 89 |
| Experiment 2 | 0 | 0 | 14 | — | 95 | 95 | — | 60 |
| Experiment 3 | 0 | 0 | — | — | 94 | 75 | — | 95 |

The data clearly demonstrate that the response of embryos to ABA treatment is age dependent. The ABA treatment to embryo at early stages of development (before 5 days) did not induce desiccation tolerance. However it is appreciated that this time varies depending on growth conditions and species.

EXAMPLE 8

Effect of Fast and Slow Drying on the Survival of Alfalfa Embryos

In this example, alfalfa embryos were formed as described and treated with ABA as in Example 6. The embryos were then subjected to "fast" drying as in Example 1 and "slow" drying. Fast drying involves a rate of water loss of about 6.7 g H20/g dry weight/day. On the slow drying treatment, embryos were placed in a series of humidity controlled chambers with progressively lower humidity over a 6 day period. The humidities used were 97, 87, 76, 63, 51 and 43% sequentially. The rate of water loss shown in Table X. approximates 1.2 g H20/g dry weight/day.

TABLE X

| Water loss from alfalfa embryos during slow drying. | | | | | | | |
|---|---|---|---|---|---|---|---|
| Rel. Humidity % | - | 97 | 87 | 76 | 63 | 51 | 43 |
| Day | 0 | 1 | 2 | 3 | 4 | 5 | 6 |
| g H$_2$O.g dry wt$^{-1}$ | - | 6.9 | 6.2 | 5.1 | 3.5 | 2.3 | 1.1 | .19 |

At the end of the drying sequence, the embryos were equilibrated in air to the same moisture content as the fast dried embryos. Viability was measured as regrowth as in Example 6.

TABLE XI

Survival of alfalfa embryos after slow and fast drying treatments

| ABA concentration u Molar | Drying Rate | |
|---|---|---|
| | Fast | slow |
| | % regrowth | |
| 0 | 15 | 44 |
| 5 | 56 | 67 |
| 10 | 65 | 57 |

Slow drying in the absence of ABA was able to confer some degree of tolerance to the embryos. Maximal survival as shown in Table XI occurred at $5 \times 10^{-6}$ M ABA with slow drying and at $10^{-5}$ M ABA with fast drying, but the effective concentration is quite broad. It is quite possible that slow drying induces the synthesis of endogenous ABA by the embryo itself.

EXAMPLE 9

Effect of Duration of ABA Exposure on Desiccation Tolerance

The duration of exposure to ABA modifies the optimum concentration and optimum stage of development of the alfalfa embryos, but this range is quite broad. To illustrate this, the effects of exposure to 3 concentrations of ABA for 5, 10, and 15 days was determined as outlined in Example 6. The drying treatments used were fast and slow drying as described in Example 7. Viability was determined as regrowth into plants.

TABLE XII

Effect of ABA concentration and duration of exposure on the survival of alfalfa embryos after fast and slow drying.

| Days of Exposure | 5 days | | 10 days | | 15 days | |
|---|---|---|---|---|---|---|
| Drying Rate | Fast | Slow | Fast | Slow | Fast | Slow |
| ABA concentration ($10^{-6}$ molar) | % regrowth | | | | | |
| 0 | 0 | 23 | 1 | 18 | 0 | 0 |
| 5 | 28 | 61 | 48 | 50 | 56 | 54 |
| 10 | 31 | 70 | 36 | 64 | 53 | 50 |

All factors which might be expected to influence the concentration of ABA inside the cells of the embryos influenced the survival following desiccation and appear to interact. The concentration of ABA in the media, the duration of exposure and the rate of drying had significant effects.

EXAMPLE 10

Effect of Environmental Stresses, Including Low and High Temperature and Deprivation of Nutrients and Water, on the Survival of Alfalfa Embryos Following Drying Many environmental stresses promote plants to synthesize ABA as noted in Walton, D.C. 1980. Biochemistry and Physiology of Abscisic Acid *Ann. Rev. Plant Physiol.* 26:775–780. Somatic embryos may respond in a similar manner. This possibility is shown by 4 separate experiments conducted using somatic embryos produced as described above and sampled 14 days after transfer to Bi2Y' media. No exogenous ABA was added. The embryos were:

a) transferred to Bi2Y' media with low levels of inorganic salts b) transferred to a cold room at 2°–4° C., 12 h photoperiod 200 uEm-1²s-1 photon flux density for a further 14 days.

c) allowed to slowly dry on the Bi2Y' agar medium by removing the parafilm seal and sampled 18–23 days later.

d) incubated at 38° C. for 10 min to 120 min.

Embryos were subsequently dried by either the "slow" or "fast" method described in Example 2, and viability assessed as regrowth into plants.

TABLE XIII

Effect of environmental stresses on survival of alfalfa somatic embryos following drying.

| Treatment | Fast Drying | Slow Drying |
|---|---|---|
| | % regrowth | |
| Control. | 16 | 27 |
| ½ Bi2Y' salts | 16 | 52 |
| ¼ Bi2Y' salts | 0 | 81 |
| 1/10 Bi2Y' salts | 0 | 14 |
| Cold stressed | 10 | 57 |
| Water stressed | 63 | 45 |
| Heat stressed at 38° C. for: | | |
| 10 min | 45 | 55 |
| 30 min | 50 | 60 |
| 60 min | 50 | 65 |
| 120 min | 58 | 59 |

The imposition of an additional stress or signal to the embryos prior to drying, especially prior to slow drying, enhanced the ability of the embryos to regrow following drying. Some of these treatments approached or exceeded the efficacy of the exogenous application of ABA and might be used in place of it as a signal to the embryo leading to the development of desiccation tolerance.

EXAMPLE 11

Effect of Triazoles on the Survival of Alfalfa Embryos Following Drying

Triazoles are groups of compounds which have plant growth regulatory properties. Some of these are know to induce an increase in ABA synthesis in plants. (E)-(P-chlorophenyl)-4,4-dimethyl-2-(1,2,4 triazol-1-yl)-1-penta-3-ol, e.g., Uniconizole (Ortho Chemical Co.) has been chosen in our experiments to represent this group of compounds, and also as a chemical agent capable of inducing ABA synthesis.

Embryos were grown as described above on Bi2Y' media and transferred to Bi2y media containing different concentrations of the triazole. No exogenous ABA was added. After 10 days embryos were dried by either the "slow" or "fast" method.

TABLE XIV

Effect of triazole treatment on the survival of embryo after desiccation.

| Uniconizole Concentration ($\times 10^{-6}$ molar) | % Regrowth | |
|---|---|---|
| | Fast dry | Slow dry |
| 0 | 3 | 34 |
| 0.1 | 35 | 45 |
| 0.5 | 25 | 40 |
| 1.0 | 30 | 35 |
| 5.0 | 25 | 40 |
| 10.0 | 46 | 57 |
| 25.0 | 45 | 35 |
| 50.0 | 45 | 49 |

Although these embryos survived and converted into plantlets the quality of plantlets were not comparable to ABA treated plants. There appears to be other effects of the triazole such as growth retarding effects. However, it is appreciated that the method can be used to improve desiccation tolerance in embryos.

EXAMPLE 12

Enhancement of Seedling Vigor in Dried Somatic Embryos

Alfalfa somatic embryos were induced as above, transferred to $10^{-5}$ M ABA media for 7 days and slow dried. Dried embryos were germinated on moist germination paper for 2 weeks. At that time, their growth was compared to somatic embryos which had been allowed to continue their development on Bi2Y' media for the same duration of time

TABLE XV

Growth and development of alfalfa seedlings from various types of somatic and zygotic embryos, after 2 weeks regrowth.

|  | Somatic Embryo | |
| --- | --- | --- |
|  | No ABA No Drying | With ABA Dried |
| Total fresh weight (mg) | 8.4 | 14.5 |
| Shoot fresh weight (mg) | 5.1 | 9.8 |
| Root fresh weight (mg) | 3.3 | 4.7 |
| Shoot length (mm) | 5.8 | 7.2 |

Drying the somatic embryos increased the growth rate of the seedlings following germination by approximately 2 fold. The enhanced vigor of the dried somatic embryo would be expected to aid in the establishment of seedlings under competitive conditions, such as those experienced in a greenhouse or field situation.

EXAMPLE 13

Comparison of the ABA Treatment During Embryo Induction Phase and ABA Treatment After Embryo Formation The basic difference between the practice of Janick and Kitto (supra) and the process described above is the stage at which the ABA treatment is imposed. The former process included ABA in the media during the embryo induction phase at which time other growth regulators were present. In contrast this process applies ABA after the induction of embryo formation has been completed when other growth regulators are absent. To compare these two processes, somatic embryos of alfalfa were induced and ABA treatment ($10^{-5}$ molar) was imposed either during induction phase in suspension where other growth regulators (2,4-D, NAA) were present or after the embryos were formed on hormone free Bi2y media. The data (Table XVI) clearly demonstrate the difference between the two processes. The ABA treatment at induction phase (in suspension) did not induce desiccation tolerance. In contrast the ABA treatment after the embryo was developed to the early cotyledon stage induced desiccation tolerance in embryos.

TABLE XVI

Comparison of the response of embryos to ABA treatment at induction phase vs ABA treatment after embryo formation.

| Treatment | | |
| --- | --- | --- |
| 10 umolar ABA during induction (in suspension) | 10 umolar ABA after embryo formation (7 day old embryos) | % survival (regrowth) |
| Yes | Yes | 64 |
| Yes | No | 4 |
| No | Yes | 78 |
| No | No | 0 |

EXAMPLE 14

Longevity of Dried Somatic Embryos in the Dry State

Dried somatic embryos can be stored using systems identical for storage of true seeds. Optimum storage of embryos would be expected to occur in cool, dry conditions. The dried somatic embryos produced in example 1 were stored in a petri dish under normal atmospheric conditions at room temperature, in a laboratory drawer. After 8 months storage under conditions which are less than optimal, there was no appreciable loss of embryo viability, i.e. regrowth of the embryos was in the order of 65-70%.

EXAMPLE 15

Induction of Desiccation Tolerance in Microspore Derived Embryos from Brassica

To illustrate that the process described herein is applicable to plant embryos in general and is not specific to alfalfa somatic embryos, desiccation tolerance has ben induced in embryos derived from Brassica microspores.

In preliminary experiments, embryos in the torpedo to cotyledonary stages of development were treated with $10^{-5}$ to $10^{-6}$ molar ABA on the agar medium using nylon screens to separate the embryos from the media. The embryos were maintained on the ABA media for 7 days and subsequently dried using the fast and slow methods. In essence, the procedure used was similar to that used for the alfalfa somatic embryos. The survival of the microspore-derived embryos was approximately 60%. Growth of non treated embryos is routinely in the 60-70% range, therefore the drying process seemed to be quite satisfactory.

TABLE XVIII

Survival of ABA treated Brassica embryos after desiccation

| ABA concentration | % regrowth | | |
| --- | --- | --- | --- |
| u moles | roots only | shoots | plantlets |
| 0 | 0 | 0 | 0 |
| 10 | 65 | 0 | 0 |
| 25 | 65 | 10 | 10 |
| 50 | 68 | 50 | 50 |

In additional experiments, embryos were induced from *Brassica napus* microspores in liquid culture as described in more detail in Pecham, P.M. and W. A. Keller. 1988. Identification of potentially embryonic microspores in *Brassica napus* L. Physiol. Plant. (in press). At 32 days, cultures were given an ABA treatment by introducing ABA directly into the solution. The culture consisted of embryos at different stages of development. The embryos were fractioned by size into two groups; 2-4 mm size representing more mature cotyledonary stage embryos and into less than 2 mm size (younger embryos). Both fractions were treated with $5\times10^{-5}$ molar ABA introduced to the solutions for 7 days. Subsequently embryos were either slow or fast dried on a mesh or on a filter paper as detailed for alfalfa.

TABLE XVIII

Survival of Brassica napus microspore derived embryos following fast and slow desiccation.

| Drying rate | No ABA | | $5\times10^{-5}$ molar ABA | |
| --- | --- | --- | --- | --- |
|  | Fast | Slow | Fast | Slow |
| Embryo size: | % viability | | | |
| <2 mm | 0 | 0 | 4 | 4 |
| 2-4 mm | 33 | 59 | 95 | 83 |
|  | % conversion to normal plants | | | |
| <2 mm | 0 | 0 | 4 | 0 |
| 2-4 mm | 0 | 16 | 40 | 37 |

The data clearly indicated that the ABA treatment improved the desiccation tolerance in Brassica embryos and this response is specific to developmental stage of the embryo. More mature embryos at cotyledonary stage responding better to ABA treatment than younger embryos.

These results are in full agreement with those obtained with alfalfa indicating the process is most likely broadly applicable to all embryos developing in vitro.

The ability to dry somatic or microspore-derived embryos will provide tremendous improvement to the current technology for the production of artificial seeds. The two main benefits are prolonged storage in a dormant state and enhanced vigour of the resultant seedling. When dry, the metabolism of the embryo is arrested and thus the utilization of valuable storage reserves, and the growth of the seedling is prevented. It is anticipated that tissue prepared and dried as described in this procedure could be stored in similar ways and for similar periods of time compared to "true" seeds. The other benefit is the enhanced vigour of the seedling produced from a dry embryo compared to that Produced by an embryo which follows a developmental path analogous to precocious germination. The reason for the enhanced vigour is not clearly defined in this instance but is probably analogous to the situation with zygotic embryos.

Some of the uses of artificial seeds for commercial purposes have been described, but the full potential has not been fully realized because of their inability to dry embryos. The applications include the following:

1. Plant tissue culture techniques and artificial seeds can be used to clone individual plants for:
   a) propagation of ornamental plants;
   b) propagation of elite germplasm, such as hybrids or parental stock in seed production;
   c) propagation of sterile plants, such as male- or female-sterile plants used in hybrid production;
   d) reducing the number of meiotic events required to produce seed of commerce where such meiotic recombination results in reduced plant performance;
   e) production of pathogen-free propagules for transport, avoiding problems and delays associated with quarantine and/or import restrictions, when that transport is across international borders.

2) Dried somatic or microspore derived embryos could also be used to store plants in a quiescent state for long or short periods of time, in situations analogous to seed storage. This has advantages for:
   a) maintaining viable stock of genetically diverse plants as in germplasm storage;
   b) maintaining a stock of elite or unique plants which are genetically heterozygous and therefore whose progeny would not necessarily have the same traits;
   c) maintaining a stock of plants until favorable planting conditions or space is available, such as in the evaluation of doubled haploids from microspore-derived embryos;
   d) maintaining a stock of plants for direct commercial sale to nurseries or growers;
   e) obtaining propagative materials for plants which do not produce seeds regularly or produce non-viable, e.g., empty seeds Although preferred embodiments of the invention have described herein in detail, it will be understood by those skilled in the art that variations may be made thereto without departing form the spirit of the invention or the scope of the appended claims.

We claim:

1. A process for inducing desiccation tolerance in a in vitro formed plant embryo to enable production of viable artificial seeds, said process comprising culturing in vitro embryos of plants that are capable of developing embryos, stimulating said embryos to proceed through globular and a heart-shaped stage into an elongate-torpedo-shaped stage and early cotyledon stage, inducing said embryos after induction of embryo formation has been completed and as early as said torpedo-shaped stage with a source of abscisic acid at an effective concentration of abscisic acid and for a sufficient period of time to cause expression of desiccation tolerance said inducing of said embryos with abscisic acid being completed before precocious germination and then drying said induced embryos to a moisture content less than about 20% by weight to provide stable viable embryos.

2. A process of claim 1, wherein said induction of said embryos with said source of abscisic acid comprises application of an environmental stress to cause said embryos to synthesize said abscisic acid in sufficient quantity to cause expression of desiccation tolerance in said embryos.

3. A process of claim 2, wherein application of an environmental stress comprises one or more of the following applications:
   i) slow gradual desiccation
   ii) low temperature
   iii) nutrient starvation
   iv) heat stress
   v) osmotic stress.

4. A process of claim 1, wherein said induction of said embryos with said source of abscisic acid comprises exogenous application of abscisic acid to said cultured embryos.

5. A process of claim 4, wherein said embryos are cultured on a support which is permeable to a culture media for said embryos, adding said abscisic acid to said media to induce said embryos.

6. A process of claim 5, wherein said support is a permeable nylon paper or mesh.

7. A process of claim 6, wherein said media is a solid agar media.

8. A process of claim 1, wherein said induction of said embryos continues 5 to 14 days.

9. A process of claim 8, wherein said abscisic acid is applied at a concentration in the range of $10^{-8}$ to $10^{-3}$ M.

10. A process of claim 8, wherein said embryos during said globular stage are screened to provide a culture of somatic embryos synchronized in their development.

11. A process of claim 10, wherein said embryos are screened through and captured between 500 um open nylon mesh and 200 um open nylon mesh.

12. A process of claim 11, wherein said embryos are derived from the group consisting of Alfalfa or Brassica.

13. A process of claim 1, wherein said drying is conducted over a span of a day.

14. A process of claim 13, wherein said induced embryos are dried at a rate of 1.2 to 6.7 g $H_2O$/g dry-weight/day.

15. A process of claim 1, wherein said source of abscisic acid is developed by inducing embryos with an inhibitor of isoprenoid metabolish, said inhibitor being (E)-(P-chlorophenyl)-4,4-dimethyl-2-(1,2,4, triazol-1-yl)-1-yl)-1-pental-3-ol.

16. A plant embryo in which desiccation tolerance has been induced by the process of claims 1, 2, 4, 8, 10, or 15.

17. A process of claim 1, wherein said embryos are derived from the group consisting of Alfalfa or Brassica.

* * * * *

UNITED STATES PATENT AND TRADEMARK OFFICE
CERTIFICATE OF CORRECTION

PATENT NO. : 5,238,835

DATED : August 24, 1993

INVENTOR(S) : McKersie et al.

Page 1 of 2

It is certified that error appears in the above-identified patent and that said Letters Patent is hereby corrected as shown below:

Title page, item [56] References Cited,
IN OTHER PUBLICATIONS:

Delete lines 20-23 [duplication]

Column 1, line 55:
"bamdoo" should be -- bamboo --.

IN THE CLAIMS:

Column 18, line 24:
"a" should be -- an --; and
"in" (second occurrence) should be -- in --.

Column 20, line 2:
"of" should be -- between --.

Column 20 line 6:
"metabolish" should be -- metabolism --.

Column 20, line 8:
"yl) -1-yl)-1-penta-3-ol" should be --yl)-1-yl)-1pental-3-01)--.

UNITED STATES PATENT AND TRADEMARK OFFICE
CERTIFICATE OF CORRECTION

PATENT NO. : 5,238,835
DATED : August 24, 1993
INVENTOR(S) : McKersie et al.

It is certified that error appears in the above-identified patent and that said Letters Patent is hereby corrected as shown below:

Column 6, TABLE I:

"$CaCl_2 \cdot 2HO$" should be -- $CaCl_2 \cdot 2H_2O$ --.

"$H_3BO^3$" should be -- $H_3BO_3$ --.

"$ZnSO_4 \cdot 7H_2)$" should be -- $ZnSO_4 \cdot 7H_2O$ --.

Column 11, line 65:
"10-3" should be -- $10^3$ --.

Column 12, line 18:
"10-5" should be -- $10^{-5}$ --.

Signed and Sealed this

Eleventh Day of October, 1994

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO. : 5,238,835

DATED : August 24, 1993

INVENTOR(S) : McKersie et al.

It is certified that error appears in the above-identified patent and that said Letters Patent is hereby corrected as shown below:

```
Column 20, line 8, "yl)-1-yl)-1-pental-3-ol" should
be -- yl)-1-penta-3-ol --.
```

Signed and Sealed this

Thirteenth Day of December, 1994

Attest:

BRUCE LEHMAN

Attesting Officer

Commissioner of Patents and Trademarks